US007232686B2

(12) United States Patent
Takayama et al.

(10) Patent No.: US 7,232,686 B2
(45) Date of Patent: Jun. 19, 2007

(54) METHOD OF NANOPATTERNING BY FORMING CRACKS IN A COATED POLYMER SUBSTRATE

(75) Inventors: Shuichi Takayama, Ann Arbor, MI (US); Xiaoyue Zhu, Ann Arbor, MI (US); Joong Hwan Bahng, Ann Arbor, MI (US); Elizabeth Ho Liu, Ann Arbor, MI (US); Jeongsup Shim, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 460 days.

(21) Appl. No.: 10/602,910

(22) Filed: Jun. 24, 2003

(65) Prior Publication Data

US 2004/0063199 A1 Apr. 1, 2004

Related U.S. Application Data

(60) Provisional application No. 60/391,123, filed on Jun. 24, 2002.

(51) Int. Cl.

| | |
|---|---|
| ***C12N 5/00*** | (2006.01) |
| ***C12N 11/00*** | (2006.01) |
| ***C12Q 1/00*** | (2006.01) |
| ***C12Q 1/02*** | (2006.01) |
| ***C07K 17/08*** | (2006.01) |
| ***C07K 17/14*** | (2006.01) |

(52) U.S. Cl. ............................ 435/395; 435/4; 435/29; 435/174; 530/811; 530/815

(58) Field of Classification Search ..................... None
See application file for complete search history.

(56) References Cited

U.S. PATENT DOCUMENTS 3,791,198 A 2/1974 Alburger
4,802,951 A * 2/1989 Clark et al. ................... 216/56

OTHER PUBLICATIONS

Joanna Aizenberg et al., Controlling Local Disorder in Self-Assembled Monolayers by Patterning the Topography of Their Metallic Supports, Nature, vol. 394, Aug. 27, 1998, pp. 868-871.

Chun-Hway Hsueh, J. Am. Ceram. Soc., 84(12), pp. 2955-2961 (2001).

Samuel Boateng et al., *Peptides Bound to Silicone Membranes and 3D Microfabrication for Cardiac Cell Culture*, Adv. Mater. 2002, 14, No. 6, Mar. 18, pp. 461-463.

Emanuele Ostuni et al., *Patterning Mammalian Cells Using Elastomeric Membranes*, American Chem. Soc., Langmuir 2000 16, 7811-7819; Jun. 21, 2000.

S. Zankovych et al., *Nanoimprint Lithography: Challenges and Prospects*, Institue of Physics Publishing, Nanotechnology 12 (2001) pp. 91-95.

S. Sun et al., "*Nanoscale Molecular Patterns Fabricated by Using Scanning Near-Field Optical Lithography*," J. Am. Chem. Soc., vol. 124, 11, 2002.

K. Lee et al., "*Protein Nanoarrays Generated by Dip-Pen Nanolithography*," Science, v. 295, pp. 1702-1705, Mar. 2002.

Hongwei Li et al., *High-Resolution Contact Printing with Dendrimers*, 2002 American Chem. Soc., vol. 2, No. 4, pp. 347-349.

Donna L. Wilson, et al., *Surface Organization and Nanopatterning of Collegen by Dip-Pen Nanolithography*, PNAS, Nov. 20, 2001, vol. 98, No. 24, pp. 13660-13664.

Emanuele Ostuni et al., *A survey of Structure—Property Relationships of Surfaces that Resist the Adsorption of Protein*, 2001 Am. Chem. Soc., Langmuir 2001, 17, pp. 5605-5620.

Emanuele Ostuni et al., *Selective Deposition of Proteins and Cells in Arrays of Microwells*, 2001 Am. Chem. Soc., Langmuir 2001, pp. 2828-2834.

Agnes R.D. et al., *Cold Plasma Induced Modification of Stainless Steel Surfaces to Reduce Baterial Biofilm Deposition*, 1998 Annual Report, pp. 31-34.

* cited by examiner

*Primary Examiner*—David M. Naff
(74) *Attorney, Agent, or Firm*—Brooks Kushman P.C.

(57) ABSTRACT

Nanopatterned devices are easily fabricated, over large surface areas when desired, by forming a multilayer article of deformable substrate, brittle layer, and coating layer, and deforming the multilayer film such that a plurality of cracks are formed therein. The cracks have different physicochemical properties than the non-cracked coating layer, and advantageously serve as attachment points for culturing microorganisms.

14 Claims, 3 Drawing Sheets

METHOD OF NANOPATTERNING BY FORMING CRACKS IN A COATED POLYMER SUBSTRATE

CROSS-REFERENCE TO RELATED APPLICATION

This application claims the benefit of U.S. provisional application Ser. No. 60/391,123, filed Jun. 24, 2002.

BACKGROUND OF THE INVENTION

1. Field of the Invention

The field of the invention pertains to for devices having patterned nanofeatures suitable for controlled cell culture and for microanalysis of protein patterns deposited thereon.

2. Background Art

Controlled cell culture and analysis of proteins on a nano scale has been achieved in the past by patterning of substrates with adherent domains suitable for receiving adherent proteins and other molecules such as DNA, RNA, etc. Prior methods have involved patterning processes typical for the production of integrated circuits and like products. However, the patterning process is relatively expensive, limited to relatively flat surfaces, and the patterns created are limited with respect to their size and spacing, and further limited in size by availability and cost of large size substrates.

For example, S. Boateng et al., "Peptides Bound to Silicone Membranes and 3D Microfabrication for Cardiac Cell Culture," ADV. MATER., 2002, 14, No. 6, pp. 461–463 discloses the use of patterned silicone elastomer substrates in in vitro cardiac mechano-biological studies. The patterned substrates are created by photolithography and consist of parallel grooves of 10 μm width and 10 μm spacing. E. Ostuni et al., "Patterning Mammalian Cells Using Elastomeric Membranes," LANGMUIR 2000, 16 pp. 7811–7819 discloses freestanding lift-off membranes having a pattern of holes, which are applied to a substrate, the substrate is treated chemically and/or biologically through the holes, and the membrane is then peeled from the substrate. The holes are on the order of 50–80 μm in size.

S. Zankovych et al., "Nanoimprint Lithography: Challenges and Prospects," NANOTECHNOLOGY 12 (2001), pp. 91–95 discloses pressure imprinting utilizing a metal-plated die master which is then pressed into a polymer above its glass transition temperature. The polymer is first cast onto silicon. Die lifetime is a problem, and the size and spacing of nanofeatures becomes increasingly problematic as size and spacing decrease below about 100 nm.

S. Sun et al., "Nanoscale Molecular Patterns Fabricated by Using Scanning Near-Field Optical Lithography," J. AM. CHEM. SOC., Vol. 124, 11, pp. 2414–2415 discloses patterning of gold surfaces treated to be covered with self-assembled monolayers by adsorption of alkanethiols, followed by programmed irradiation employing a U.V. laser source and a scanning near-field optical microscope. Line widths of 40 nm were routinely achieved. While small device features are achievable, the method is time-consuming and limited with respect to substrate.

K. Lee, et al., "*Protein Nanoarrays Generated by Dip-Pen Nanolithography*," SCIENCE, V. 295, pp. 1702–1705, discloses patterning of gold plated substrates by depositing dots or grids of 16-mercaptohexadecanoic acid onto the substrate, followed by passivation of surrounding areas with 11-mercaptoundecyl-tri(ethylene glycol). Proteins could be absorbed on the active areas by immersion into an aqueous solution of protein. This process is limited in scope due to the necessity of employing gold plated substrates, and requires complex control of the deposition apparatus.

It would be desirable to provide a method for nanopatterning which can be applied to substrates of large surface area, on planar, non-planar, or even three-dimensional surfaces, which does not rely on typical patterning methods for its production, and which can be effected at reasonable cost.

SUMMARY OF THE INVENTION

The invention provides a process for providing a nanopatterned substrate, comprising providing a flexible and/or elastomeric substrate, forming a brittle layer on a surface of the substrate, providing a coating layer of defined physicochemical properties on the brittle layer, straining the brittle layer to provide cracks which expose portions of brittle or substrate layers not covered with the coating layer. Proteins and other molecules for which culture and/or analysis is contemplated can subsequently be applied to the substrate and will adhere to exposed adherent portions in the cracks of the uppermost layer.

DETAILED DESCRIPTION OF THE PREFERRED EMBODIMENTS

Figures 1A, 1B, 1C:
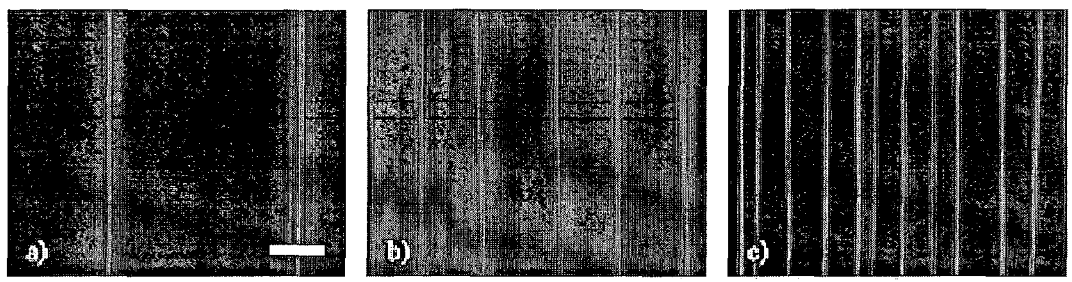
FIGS. 1*a*–1*c* illustrate parallel nanocracks made in a device of the subject invention at different degrees of strain.

In its broadest form, the present application involves providing a flexible and/or elastomeric substrate, providing a brittle surface on the substrate, coating the substrate with a layer which is preferably non-adherent with respect to the particular substance, e.g., biological organisms, etc., later to be applied, and deforming the substrate and the brittle layer in such a manner that a plurality of cracks are developed in the outermost layers which penetrate to expose surfaces which are adherent or can be treated to be adherent to the molecules or organisms under consideration. The brittle surface and the coating layer preferably constitute separate layers.

In one embodiment of the invention, the devices of the subject invention exhibit a difference in physicochemical properties between the non-cracked surface of the devices and the cracks or trenches of the device with respect to molecules or microorganisms of interest, by treating at least one of the surface and/or the cracks with a treating agent which alters its physicochemical properties with respect to the other. For example, the brittle surface may be intrinsically hydrophilic, and be coated, prior to cracking, with a hydrophobic substance. In the case of silaceous brittle coatings, for example, the surface is easily hydrophobicized by silylating with conventional silylating agents. After cracking, non-silylated silaceous material will be exposed, or the substrate itself may be exposed, depending upon the depth of the cracks.

In like manner, a hydrophobic brittle layer, for example one of alkylsilicone resin, may be reacted with a silylating agent which bears hydrophilic groups, such as a polyaminopolyalkylenetrialkoxysilane, a glycosidyl trialkoxysilane, or a polyoxyalkylenetrialkoxysilane, to produce a hydrophilic surface. Following cracking, hydrophobic cracks will be exposed. In either case, the cracks, with their different characteristics relative to the uncracked surface, can be further treated with other treating agents, while the uncracked surface will retain different physicochemical characteristics.

Treating agents which prevent cell attachment, i.e., bovine serum albumin, are particularly useful for coating the surface prior to cracking. Such treatments minimize or prevent cell attachment on the treated surfaces. The cracks may be untreated, or may be treated with substances which, e.g., promote cell attachment. In this manner, it is possible to plate cells along the cracks. Parallel nanolines have been proven useful in cell growth and manipulation, since they mimic the patterns of extracellular protein seen in vivo. Thus, such nanopatterned substrates should prove of great utility in generation of nanolines of ECM ("extra cellular matrix") proteins and other trophic factors over wide areas, for uses in tissue engineering and cell-based assays. It is also possible to pattern insoluble growth factors such as biotinylated EGF into the nanocracks by biotin-streptavidin-biotin sandwich assay.

In addition to biological applications, the nanopatterned devices are also useful for patterning any material which has differing affinities for the non-cracked surface and the cracks. Stacks of nanopatterned devices may be created to mimic three-dimensional biological matrices, i.e., those which occur in bone marrow and the like.

The subject devices thus minimally contain three layers: a deformable substrate; at least one brittle layer on at least one surface of the deformable substrate, and at least one coating layer on the brittle layer. The coating layer will have different physicochemical properties, inclusive of biological properties, than the brittle layer. Such physicochemical properties include, but are not limited to hydrophilicity, hydrophobicity, surface energy, polarity, type of reactive surface groups, material of construction, etc.

The deformable substrate must be deformable to the extent that cracks can be generated in the brittle layer upon deformation, e.g. by stretching and/or bending. For brittle layers which are highly brittle, i.e., displaying low cohesiveness, the substrate may be only marginally deformable. In such cases, thermoplastics such as polyamides, polyethylene, relatively hard silicone elastomers, etc., may be used, since even modest stretching or other deformation will cause the brittle layer to crack. With brittle layers of greater cohesiveness, the substrate may be a softer material, for example a PDMS elastomer, a polyurethane elastomer, etc. In some cases, extensible metal foils may serve as the substrate. The brittle layer may be immediately adjacent the deformable substrate, or may be isolated therefrom by one or more additional layers.

Preferred deformable substrates are organopolysiloxanes which are easily oxidized at their surface to generate silaceous coatings, i.e., coatings with a high content of $RSiO_{3/2}$ and especially $SiO_{4/2}$ groups, where R is hydrocarbon, alkoxy, hydroxyl, etc. Organopolysiloxane elastomers with residual reactive groups such as silanol, silicon-bonded hydrogen, alkoxy, etc., may also be treated with silicone resins or tri- or tetra-functional silylating agents to form either an intrinsically brittle layer or one which can be easily embrittled by oxidation or further chemical reaction. In like manner, other elastomers bearing functional groups may be reacted with orthosilicates or silicone resins to form intrinsically brittle or oxidizable and embrittable layers.

The substrate is preferably an elastomeric substrate, and most preferably, an elastomeric substrate composed of a polyorganosiloxane polymer. The surface of the substrate must be rendered brittle with respect to the brittleness of the substrate itself. With polysiloxane substrates, for example, this brittleness may be imparted by controlled oxidation of the substrate in a plasma environment. In the case of other substrates, particularly those of polymers which are cured to an elastomer but which have unreacted polymerizable groups, these polymerizable groups may be polymerized at the surface, crosslinking the surface and producing a brittle polymer surface layer. For example, the substrate may consist of a condensation polymerizable substrate wherein the polymerizable molecules contain numerous unsaturated groups. The polymer may contain or may be treated to contain on its surface, a suitable photoinitiator which, when exposed to high energy radiation such as ultraviolet light, causes extensive crosslinking only at the surface of the polymer. The flexible substrate may also be coated with an adherent but brittle coating overlying the flexible substrate. The method of providing the brittle layer is not critical, and it may be characterized as a layer which has physical properties with respect to the deformable substrate that the brittle layer will crack as the substrate is deformed.

In a preferred embodiment, a polysiloxane is oxidized, forming a brittle layer, and this brittle layer is then reacted with a hydrophobicizing substance such as perfluorooctyltrichlorosilane, tridecafluoro-1,1,2,2-tetrahydrooctyl-1-trichlorosilane, propyltrichlorosilane, or triethoxypropylsilane to render the brittle surface hydrophobic. Substantially any reactive chlorosilane or alkoxysilane may be used, as well as other hydrophobicizing substances such as hexamethyldisilazane. Making the surface hydrophobic is not necessary for all purposes, but is used in preferred embodiments prior to rendering the surface non-adherent to cellular organisms. Instead of making the surface hydrophobic, the surface may be made directly resistant to protein adsorption. The hydrophobic surface, when used, may be coated with a substance which renders proteins and other molecules non-adherent, such as Bovine Serum Albumin (BSA). Following preparation of the non-adherent coating over the substrate, the substrate is then flexed and/or stretched, generating cracks which extend through the non-adherent layers such as the bovine serum albumin and hydrophobic coating layers, exposing a fresh, adherent surface.

When oxidation of PDMS substrates is employed to create the brittle layer, the crack spacing and other properties may also be altered by varying the degree of oxidation, particularly the time of oxidation. In many cases, the line spacing may exhibit a minimum at a particular oxidation time, with spacing increasing with both shorter and longer exposure to the oxidizing plasma, as illustrated hereafter in Example 5. The reason for this behavior is not clear, but may be due to competing physical properties: an increased flexibility of the brittle layer produced with short oxidation times due to the thinness of the layer; and increased cohesiveness of thicker layers produced by longer oxidation.

Silanization of surfaces, when desired, may be accomplished by standard techniques, i.e., by exposure to a vapor of silylating agent. One technique which has been used successfully is to prepare a 1:1 by volume mixture of mineral oil and silylating agent, and place a small quantity of this mixture 2 to 3 cm below the surface to be silylated. Heat may be applied to volatilize the silylating agent, or a vacuum, e.g. 50–200 torr may be applied, or combinations of heat and vacuum, depending upon the volatility of the silane. Higher and lower pressures may be used as well. In general, preferred pressures range from 10 to 1000 torr. In a preferred embodiment, PDMS slabs are silylated for seven minutes in a vacuum chamber at 100 torr. The vacuum is strengthened and released three times at the beginning and in the middle of the procedure. When propyltrichlorosilane is used as the silylating agent, some moisture is desirably present. Such moisture can be introduced into the vacuum chamber by means of a wet adsorbent material placed in the chamber, e.g. a wet paper towel.

Other surface treatments may of course be used. Surfaces, either within the cracks or therebetween may be rendered protein-resistant by coating with surfactants, particularly block non-ionic polyether surfactants. Such surfactants contain at least one hydrophobic block composed of residues of a higher alkylene oxide, i.e. propylene oxide, 1,2-butylene oxide, 2,3-butylene oxide, oxetane, tetrahydrofuran, $C_{6-18}$ α-olefin oxides, etc., and at least one hydrophilic block composed primarily of ethylene oxide, optionally with a minor portion of a second alkylene oxide such as propylene oxide. Numerous such surfactants are available commercially, for example those of BASF Corporation designated as PLURONIC® polyether surfactants. A preferred surfactant, for example, is PLURONIC® F108 polyether surfactant. The surfactant may be applied from aqueous solution, alcoholic solution, from other solvents, or from solvent mixtures, as desired. For example, aqueous or ethanolic solutions containing 1%, 4%, 10%, and 20% by weight surfactant can be employed. If coated on the brittle layer prior to cracking, such treatment ensures that proteins, cells, etc., adhere to the crack surfaces and not to the surrounding areas. The surface, prior to treatment with the surfactant, may be oxidized, silanized, non-silanized, etc.

The formation of cracks in the surface may be performed by stretching the substrate when the substrate is either elastomeric or has a suitable elongation at break, or may be formed by passing the side of the substrate most remote from the brittle surface over a sharp knife edge, blunt round cylinder or like surface, producing tension on the outer brittle surface layer, thus creating cracks. By adjusting the radius of the knife edge or other deforming surface, the flexibility of the surface, the thickness of the substrate, and/or the elastomeric nature of the substrate, a pattern of substantially parallel surface cracks may be developed with an adjustable range of spacing. By repeating this process in a direction at an angle to the original deformation, preferably transverse, a second series of cracks can be developed at an angle to those first produced. Cracks having a circular pattern may be generated by stressing the brittle layer by means of a tip such as a needle, generating cracks which form in radially concentric circles. Stretching the substrate, e.g. bidirectionally, generates for the cracks which emanate radially away from the point of deformation, between the circular array of cracks. Many geometric variations are possible. The result is a matrix of parallel, crosshatched, radial, or even random cracks, etc., which may be used to adhere proteins, DNA molecules, RNA molecules, microtubules, viruses, stem cells, etc. Cracks formed at different times may be treated differently with chemical and/or biological agents, thus forming two series of cracks having different surface and/or physiochemical properties.

The spacing and width of the cracks may be altered by changing the nature of the substrate, by changing the percentage of strain, by changing the rate of strain, or by changing the nature of the brittle layer, e.g. by changing the oxidation time when siliceous brittle layers are formed on PDMS substrates. By percentage of strain is meant the percentage of elongation, i.e., the difference between the stretched and unstretched length divided by the unstretched length, and expressed as a percentage. The pattern may also be altered by forcing the film to traverse an edge of relatively sharp radius, as previously indicated. The use of a knife edge or the like in conjunction may facilitate greater uniformity or non-uniformity in the spacing of the cracks, as desired, particularly when the region at and beyond the knife edge experiences greater strain than the area before the knife edge.

Figure 5:
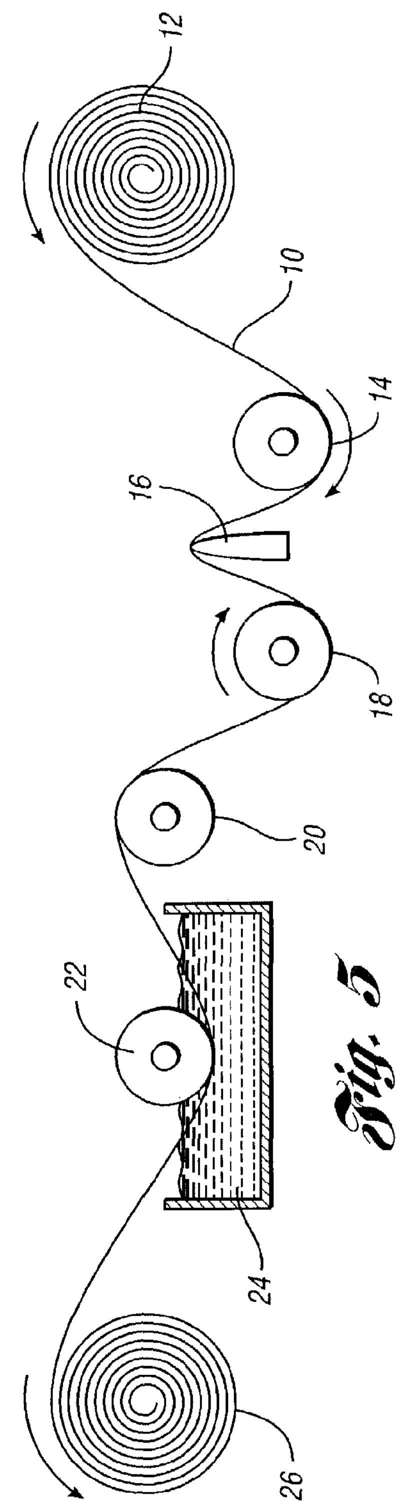
FIG. 5 illustrates a continuous method for preparing a ribbon of nanocracked multilayer film.

For example, in FIG. 5, a continuous ribbon of a deformable substrate 10 coated with a brittle material is supplied in roll form from roll 12 and is urged onward by a Godet roll 14 over knife edge 16. Godet roll 18 rotates at a higher rate than Godet roll 14, thus stretching the substrate. The strain imposed is highest between the knife edge 16 and Godet roll 18 due to friction between the substrate and the knife edge. As the substrate passes over the knife edge, cracks parallel to the knife edge will develop. Redirecting rollers 20, 22 maintain tension as the substrate, now having cracks in its brittle coating, passes through one or more treatment areas, in this case bath 24. The product is wound up on takeup roll 26.

The spacing and width of the cracks may be developed empirically, and their pattern easily altered by manipulating the elastomeric nature of the substrate, the degree and rate of strain, etc. The cracking may also be calculated roughly in advance, for example by the mathematical model disclosed by Chun-Hway Hsueh, "Analyses of Multiple Film Cracking in Film/Substrate Systems," J. Am. Ceram. Soc., 12 2955–61 (2001).

Suitable substrates include any polymer on which a brittle surface can be formed or deposited, and which provides suitable flexibility and/or elastomeric capability for generation of cracks ranging from nano to microscale. Suitable flexible substrates include, for example, polyurethanes, polyureas, polyorganosiloxanes, polyesters, polyamides, and the like. If a brittle surface layer is to be formed from the polymer itself, the polymer should be capable of degradation and/or crosslinking under suitable conditions to form a brittle surface on the polymer. The brittleness of the surface must be such in comparison with the nature of the substrate itself, that upon flexing or stretching micro- and nanocracks can be formed. For example, a polyurethane substrate may be produced by the casting of an isocyanate terminated polyoxyalkylene ether prepolymer and an amine or hydroxylfunctional chain extender, at least one of the prepolymer and/or chain extender containing moieties having ethylenic unsaturation which are subsequently crosslinkable by plasma, electron beam, or ultraviolet light. If crosslinking by ultraviolet light is to be performed, the substrate preferably contains a photoinitiator such as those provided by Ciba-Geigy under the trade name IRGACURE™. Alternatively, the photo initiator may be absent from the substrate, and the substrate may be briefly immersed in a solvent-based solution containing a photo initiator, which then penetrates only the surface of the polymeric substrate. Such polymeric substrates which include not only polyurethanes as previously described, but also polyester, polyamide, and other polymeric substrates, are then exposed to ultraviolet light which causes extensive crosslinking at the surface, but which either due to the duration and intensity of the light, presence or absence of light absorbing or light misdirecting fillers in the polymer, or the presence of the photoinitiator in only the surface of the substrate, fails to cause extensive crosslinking below surface. This surface may then be treated with hydrophobicizing agents, if necessary, with protein adherent-interfering substances such as BSA, and the like.

Another advantageous feature is the ability to generate features on non-planar substrates and even three dimensionally. An application of such products would be for tissue engineering. For example, microfluidic channels may be cracked, either longitudinally or transverse to the channel direction, allowing for cell growth, differentiation, proliferation, etc., to be studied under dynamic or steady state flow conditions.

Figure 6:
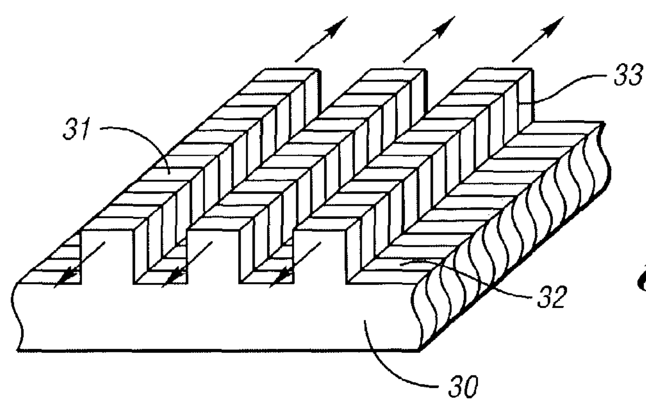
FIG. 6 illustrates a three dimensional device having a pattern of nanocracks thereon.
Figure 8:
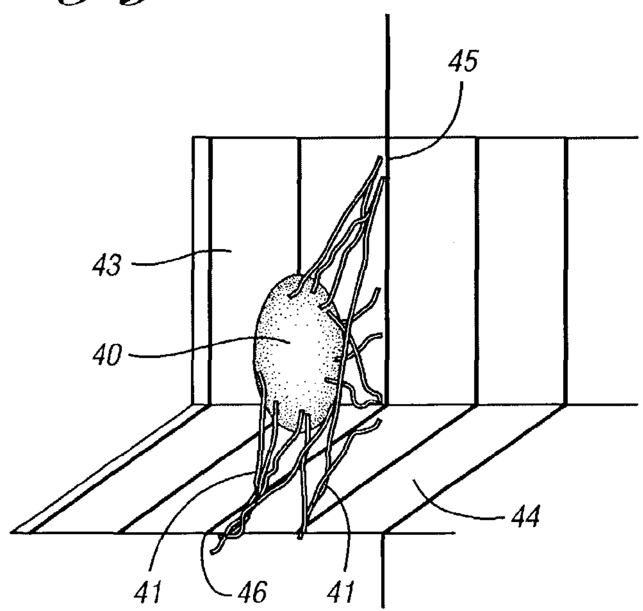
FIG. 8 illustrates cell adhesion to nanocracks of the device of FIG. 6.

An example of a three dimensional substrate is shown in FIG. 6. A PDMS substrate 30 is created with a series of ridges 31 and groves 32, here shown as rectangular in shape, although any geometric shape, e.g. triangular, semicircular, trapezoidal, etc., is possible. The PDMS substrate is oxidized to form a brittle layer on its surface, as described elsewhere, and then stretched in a direction parallel with the ridges and grooves, creating a series of transverse microcracks 33. Multiple layers may be stacked, presenting a three dimensional pattern of anchors for cell growth, etc. Cell growth on a three dimensional nanofeatured substrate such as that of FIG. 6 is shown in FIG. 8, where the cell 40 is attached to walls 43,44 by means of anchors 41 to nanocracks 45,46.

Other substrates are useful in addition to polymer substrates, and other coatings are useful as well. For example, metal on metal, ceramic on metal, and other material combinations with mechanical property mismatches will generate small cracks, the crack size depending on a variety of parameters such as a thickness of brittle layer compared to underlying layer, etc.

As indicated, the patterns generated by use of the subject invention have numerous uses. In addition to those discussed previously, the criss-cross patterns which are easily generated are useful for studying the pathfinding characteristics of cells. For example, in neuroscience, cancer metastasis, and tissue engineering development studies, it is crucial to establish how cells move around. Cell movement is usually the result of a combination of different adhesive signals and growth factor signals which cells “read”. Crossing crack patterns which have one type of protein or other surface characteristic in one direction, and another in the “cross” direction are useful in studying which direction a cell prefers and preferentially attaches to, migrates, proliferates, differentiates on, etc. Such patterns may easily be created by the present invention by creating a first series of microcracks in a given direction, coating these cracks appropriately, if necessary, and then creating a second series of cracks in another direction, this second series of cracks being coated to obtain different surface characteristics.

In addition to providing series of cracks with different surface characteristics, it is also possible to adjust the width of the cracks after their initial generation. By first cracking, then stretching (preferably after a first period of relaxation (i.e. stress relief)), the substrate may be maintained in a stretched state to broaden the crack width, or relaxed partially or totally to narrow the width, even with cells attached. Cell behavior can thus be dynamically controlled. Since cell proliferation may be dependent on the environmental dimensions, the devices may be used as a cell proliferation switch, with minimal or no proliferation while the crack width is small, followed by broadening the crack width to encourage proliferation by stretching the substrate.

The nanopatterned devices of the subject invention also have potential uses as serum-free culture systems suitable for the analysis of cell behavior, particularly cell adhesion onto the nanocracks, and the extracellular proteins involved in cell attachment. Multiple types of media, cells and proteins have been explored. It is anticipated that some such systems will also include growth factors such as epidermal growth factor (EGF).

As culture media, the following have been utilized: serum-free DMEM media (Invitrogen) with 1% BSA (Sigma) and 1% Penicillin G (Sigma), serum-free DMEM media with 1% BSA, 1% Penicillin G, and 10 μg/mL insulin (Sigma), serum-free DMEM media with 1% BSA, 1% Penicillin G, and 10 μg/mL L-α-lisophosphatidic acid (abbreviated as LPA, Sigma), serum-free DMEM media with 1% BSA, 1% Penicillin G, 10 μg/mL insulin, and 10 μg/mL LPA.

For surface treatment of the cracks, success has been experienced with Concanavalin A, Alexa Fluor® 594 conjugate (Molecular Probes); Concanavalin A, Alexa Fluor 488® conjugate (Molecular Probes); Concanavalin A, biotin-XX conjugate (Molecular Probes), streptavidin (Molecular Probes), Dextran fluorescein and biotin (Molecular Probes), fibrinogen from human plasma, Alexa Fluor® 488 conjugate (Molecular Probes), Albumin, biotinamidocaproyl labeled bovine (Sigma), Albumin, α-D-mannopyroanosylphenyl isothiocyanate bovine (Sigma), laminin, proteins contained in serum media. Potentially all kinds of proteins can be patterned into the cracks.

Numerous types of cells can be cultured or studied on the nanolines of the subject invention, for example C2C12 cells (ATCC) and prestarved C2C12 cells, neuroblastoma cells, breast cancer cell lines, and 3T3 cells (ATCC).

The subject invention devices are also suitable for sandwich assays where nanocracks are coated with a first protein, a second selective protein then binds to the first protein, and binding is confirmed by visual or machine inspection using a fluorescent polymer which is selective to the second protein, e.g. biotin, streptavidin, biotin; mannose, concanavalin A, mannose. Streptavidin may be useful for binding biotinylated growth factors onto the nanolines in addition to extracellular matrix proteins. Cross-talk between adhesive protein signaling and soluble growth factor signaling can be investigated, and used for controlling cell growth and differentiation.

Prior methods of generating patterned devices are disclosed in: Samuel Boateng et al., *Peptides Bound to Silicone Membranes and* 3D *Microfabrication for Cardiac Cell Culture*, Adv. Mater. 2002, 14, No. 6, March 18, pp. 461–463; Emanuele Ostuni et al., *Patterning Mammalian Cells Using Elastomeric Membranes*, American Chem. Soc., *Langmuir* 2000 16, 7811–7819; Jun. 21, 2000; S. Zankovych et al., *Nanoimprint Lithography: Challenges and Prospects*, Institute of Physics Publishing, *Nanotechnology* 12 (2001) pp. 91–95; Hongwei Li et al., *High-Resolution Contact Printing with Dendrimers,* 2002American Chem. Soc., Vol. 2, No. 4, pp. 347–349; Shuqing Sun et al., *Nanoscale Molecular Patterns Fabricated by Using Scanning Near-Field Optical Lithography*, J. Am. Chem. Soc., Vol. 124, No. 11, 2002; Donna L. Wilson, et al., *Surface Organization and Nanopatterning of Collegen by Dip-Pen Nanolithography*, PNAS, Nov. 20, 2001, Vol. 98, No. 24, pp. 13660–13664. Surface modification to render cell cultures, proteins, and other molecules of interest adherent or non-adherent are disclosed in Emanuele Ostuni et al., *A survey of Structure—Property*

*Relationships of Surfaces that Resist the Adsorption of Protein,* 2001 AM. CHEM. SOC., *Langmuir* 2001, 17, pp. 5605–5620; Emanuele Ostuni et al., *Selective Deposition of Proteins and Cells in Arrays of Microwells,* 2001 AM. CHEM. SOC., *Langmuir* 2001, 17, pp. 2828–2834; Agnes R. D. et al., *Cold Plasma Induced Modification of Stainless Steel Surfaces to Reduce Bacterial Biofilm Deposition,* 1998 ANNUAL REPORT, pp. 31–34. Controlling local disorder in self-assembled monolayers is described in Joanna Aizenberg et al., *Controlling Local Disorder in Self-Assembled Monolayers by Patterning the Topography of Their Metallic Supports*, NATURE, Vol. 394, 27 Aug. 1998, pp. 868–871. Adjustment of crack spacing has been studied as a theoretical problem in multiple-layer composite structures: Chun-Hway Hsueh, J. AM. CERAM. SOC., 84[12], pp. 2955–61 (2001). All of the above references form a part of the background art, and are all incorporated in their entirety by reference.

The subject invention may be illustrated by the following Examples.

EXAMPLE 1

An elastomer slab measuring 3 cm×3 cm×1 mm is cast from polydimethylsiloxane elastomer, SYLGARD® 184 (Dow Corning Corp.) according to the manufacturer's instructions, and oxidized for six minutes at 100 W at 100 mTorr in a PlasmaPrep™ II plasma etcher (SPI Supplies) to generate a thin surface film of silica-like material. The surface is then hydrophobicized by contact with perfluorooctyltrichlorosilane for five minutes. The hydrophobicized surface is then treated with bovine serum albumin (20 mg/mL) for twenty minutes, followed by washing with water. The substrate is then uniformly stretched at various percentages of strain, by adhering the slab to two spaced glass cover slips leaving a separation of 1 cm, and stretching on a stretcher provided by Scholar Tec Corp., Osaka, Japan. A pattern of parallel cracks developed, with spacing determined by the percentage strain, as shown in FIGS. 1*a*–1*c*.

Figure 2:
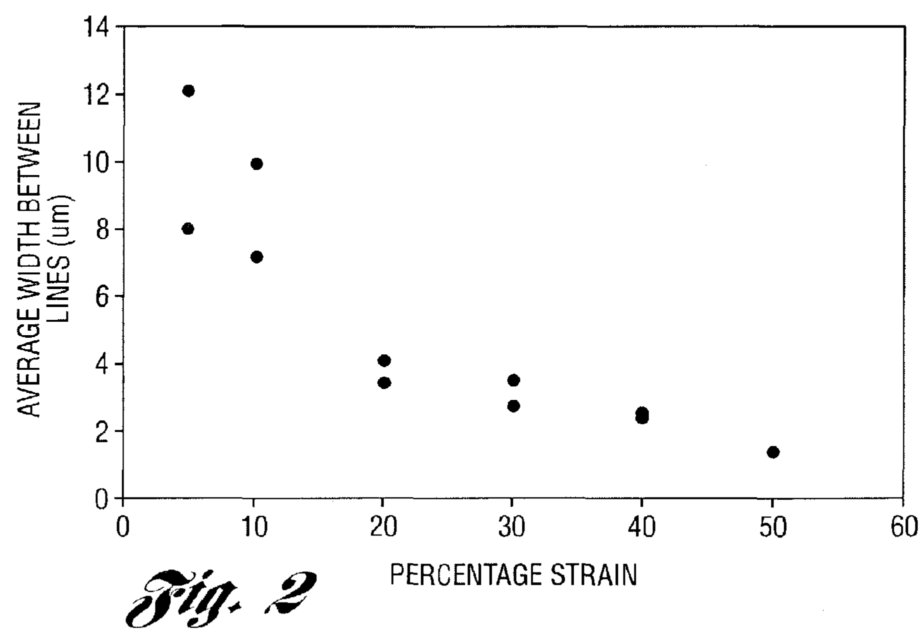
FIG. 2 illustrates one relationship between strain and nanocrack spacing.
Figure 3:
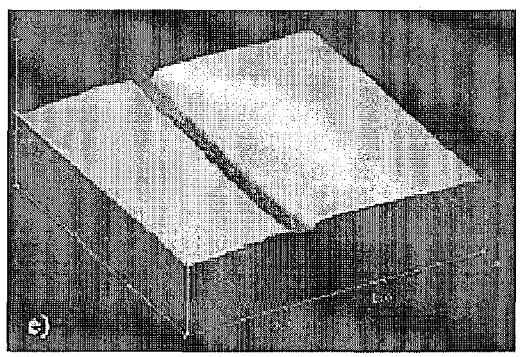
FIG. 3 illustrates the shape of a nanocrack or "trench" formed by the subject invention process.

In FIGS. 1*a*–1*c*, patterns obtained at strain rates of 5%, 30%, and 50% are shown. FIG. 2 illustrates the relationship between percentage strain and line spacing achieved with similarly prepared samples. FIG. 3 illustrates the line (crack) shape as determined by Atomic Force Microscopy (AFM). The horizontal width of the trench is 102 nm and the vertical depth 8.5 nm in this example. The exposed crack surfaces may be exposed to a different surface active/bioactive material such as DQ collagen Alexa 488 (0.05 mg/mL) for two minutes, followed by washing and releasing tension.

EXAMPLE 2

Figure 4:
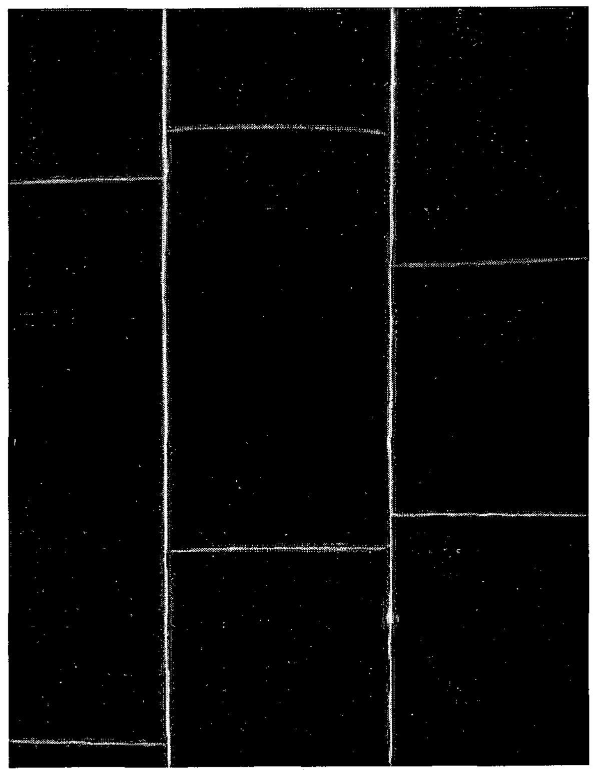
FIG. 4 illustrates bidirectional nanocracks obtained by bidirectional stretching.

The nanopatterned PDMS slab of Example 1 is stretched in a direction transverse to the original direction of stretching. The nanopattern which results is illustrated in FIG. 4.

EXAMPLE 3

Two 3 cm×3 cm×1 mm PDMS slabs are prepared as in Example 1. In one slab, a central 1 cm×1 cm square opening is cut, and the two slabs stacked together and sealed by conformal contact. The bottom surface of the well thus formed is plasma oxidized and silanized and the square well is filled with fluid, e.g., water, and stretched as in Example 1. By this technique, drying of the nanopatterned surface is avoided. Instead of water, the liquid may advantageously be a cell culture, protein solution, etc., which can directly interact with the surfaces of the nanocracks as the latter are formed. Denaturing of proteins and adsorbtion of unwanted background proteins is thus avoided.

EXAMPLE 4

Figure 7:
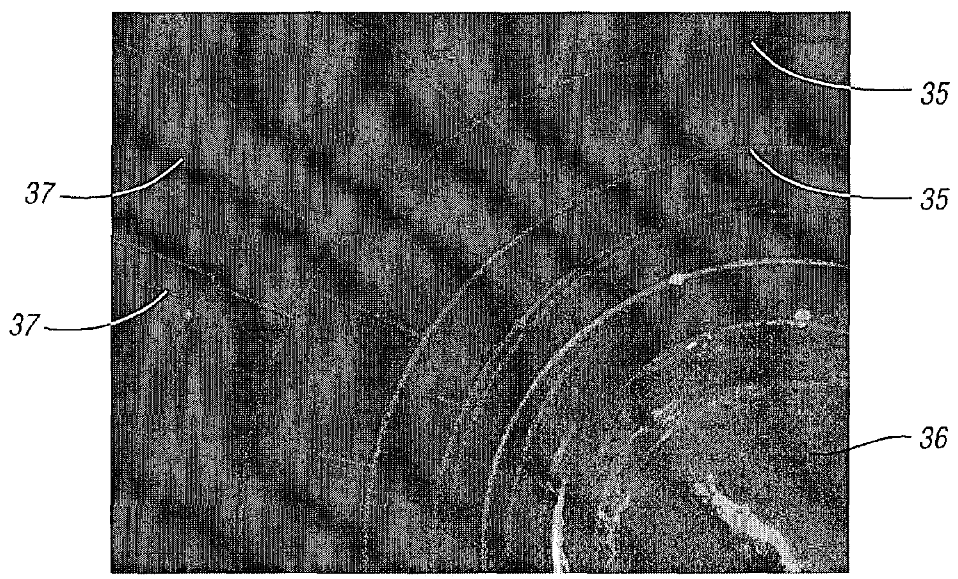
FIG. 7 illustrates a device of the subject invention having concentric circular and radially extending nanofeatures.

A PDMS substrate is prepared in accordance with Example 1 and oxidized to create a brittle surface. The surface is treated with a solution of 20 mg/mL BSA for approximately 40 minutes. The substrate is then deformed over a needle, generating a series of concentric cracks 35 spaced radially from the position 36 of the needle, as shown in FIG. 7. These cracks are then treated with a first protein solution to form cell-adherent surfaces. The substrate is then stretched biaxially, creating a series of radial cracks 37, which are then treated with a different protein solution. The resulting nanofeatured substrate contains cracks emanating in different directions, with surfaces of differing nature. In FIG. 7, the circular cracks are fluorescently labeled fibrinogen and the straight cracks are fluorescently labeled TRITC-BSA.

EXAMPLE 5

PDMS slabs measuring 2.5 mm by 2.5 mm by 1.5 mm are prepared as in Example 1, and plasma oxidized at 100 mTorr for 20 seconds, 1 minute, 4 minutes, and 16 minutes, respectively. The samples are uniaxially stretched and the crack spacing examined. The slab oxidized for one minute is found to have the densest crack spacing, with slabs of both shorter and longer oxidation times exhibiting larger average spacing between the cracks.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for nanopatterning a coated polymer substrate, comprising:

a) supplying a multilayer article comprising a deformable polymer substrate, a brittle layer adjacent said deformable polymer substrate, and a coating layer adjacent said brittle layer on a side of said brittle layer remote from said deformable polymer substrate;

b) exerting a strain on said multilayer article such that cracks develop in said brittle layer, exposing surfaces in said cracks having no coating layer thereon.

2. The method of claim 1, wherein said step of exerting a strain comprises unidirectionally stretching said multilayer article.

3. The method of claim 1, wherein said step of exerting a strain comprises bending said multilayer article.

4. The method of claim 1, wherein said step of exerting a strain comprises stretching said multilayer article in at least two directions.

5. The method of claim 1, wherein said polymer substrate comprises a polyorganosiloxane elastomer and said brittle layer comprises an oxidized polyorganosiloxane.

6. The method of claim 5, wherein said coating layer comprises a hydrophobic coating.

7. The method of claim 5, wherein said coating layer comprises a first, hydrophobic coating, and a second coating on said first coating, said second coating comprising a substance which prevents attachment of biological organisms.

8. The method of claim 5, further comprising coating said exposed surfaces with a coating which has different surface characteristics than said coating layer.

9. The method of claim 8 wherein said coating comprises at least one protein.

10. The method of claim 5, wherein said oxidized polyorganosiloane layer is formed by oxidizing a surface of said polyorganosiloxane substrate.

11. The method of claim 1, wherein said step of exerting a strain comprises stretching said multilayer article in at least two directions sequentially.

12. The method of claim 11, wherein following stretching in one direction, a coating is applied to exposed surfaces of cracks generated, prior to stretching in another direction.

13. The method of claim 1, where said coating layer is a surfactant layer.

14. The method of claim 13, wherein said surfactant is a non-ioinic polyether surfactant.

* * * * *